United States Patent [19]
Honeycutt et al.

[11] Patent Number: 5,181,966
[45] Date of Patent: Jan. 26, 1993

[54] HOT WATER SOLUBLE PACKAGING MATERIALS

[76] Inventors: Travis W. Honeycutt, 3544 Mill Rd., Gainesville, Ga. 30504; Robert L. Taylor, Jr., 130 May Glen Way, Roswell, Ga. 30076

[21] Appl. No.: 907,777

[22] Filed: Jun. 30, 1992

Related U.S. Application Data

[63] Continuation-in-part of Ser. No. 803,096, Dec. 5, 1991, which is a continuation-in-part of Ser. No. 683,290, Apr. 10, 1991.

[51] Int. Cl.$^5$ .......................... B08B 7/00; C11D 17/00
[52] U.S. Cl. .......................................... 134/42; 252/90
[58] Field of Search ............................... 134/42; 252/90

[56] References Cited

U.S. PATENT DOCUMENTS 3,859,125  1/1975  Miller et al. ........................ 428/511

*Primary Examiner*—Theodore Morris
*Assistant Examiner*—Zeinab El-Arini
*Attorney, Agent, or Firm*—Malcolm B. Wittenberg

[57] ABSTRACT

A water soluble package and its method of disposal. The package is provided with thermoplastic polymer side walls which are capable of dissolving in water and aqueous solutions only at temperatures above approximately 37° C.

7 Claims, No Drawings

HOT WATER SOLUBLE PACKAGING MATERIALS

RELATED APPLICATIONS

This Application is a continuation-in-part of U.S. application Ser. No. 07/803,096, filed Dec. 5, 1991, which is in turn a continuation-in-part of 07/683,290, filed Apr. 10, 1991 both applications are still pending.

TECHNICAL FIELD OF THE INVENTION

The present invention involves water-soluble packaging and a method of disposing of such packaging after use. Specifically, the packaging is composed of thermoplastic polymer which is water soluble only at temperatures above approximately normal human body temperature of 37° C.

BACKGROUND OF THE INVENTION

Hospitals and other patient care facilities generate considerable quantities of medical packaging mostly in the form of plastics. It is recognized that most plastic packaging materials do not biodegrade in a reasonable period of time. As such, in 1990, 36 state legislatures introduced more than 350 bills restricting plastics use. States enacted 54 other plastics laws and local governments contemplated hundreds of other measures.

In addition to the above, the potential for biohazard contamination make medical packaging difficult to recycle. Some hospital procedures on contamination control encourage multiple-barrier packaging. Fear of infection and cross contamination has encouraged the use of disposables. In 1987, health-care manufacturers produced 559 million pounds of medical product packaging. In 1992, that number may reach 821 million pounds. Ensuring sterility and device safety makes source-reduction solutions all the more challenging.

The need for an effective way to dispose of medical waste has been highlighted by the amendment made by to 29 C.F.R. §1910.1030 which provides for the federal regulation under the Occupational Safety And Health Act, 29 U.S.C. 655, 657 to control bloodborne pathogens. Specifically, the Act calls for the establishment of an exposure control plan, the containment of specimens of blood or other potentially infectious materials and the general tightening of precautionary measures to minimize the spread of disease. A safe and effective way to dispose of hospital waste in the form of used packaging would greatly facilitate compliance with the above-referenced Act.

Consumption of medical disposable products has been growing at a rate of approximately 10% a year. In 1988, sales totaled approximately 1.155 Billion Dollars. It is projected that by 1992, sales of medical disposable non-woven products will reach 1.54 Billion Dollars.

Although there is clearly a benefit in the use of disposables in the medical arts by avoiding the necessity of human contact with medical waste which is necessary in the cleaning of comparable reusables, non-biodegradable disposables are posing problems which are only now being recognized. Landfill sites are becoming increasingly burdened with disposable packaging which does not biodegrade for hundreds of years, if ever. If landfill sites become fully exploited, new sites must be found which are rightfully opposed by residents located proximate disposal site locations.

It is thus an object of the present invention to provide packaging which is capable of being disposed of after use while avoiding additional burdens being placed on landfill disposal sites.

It is yet a further object of the present invention to provide packaging and its method of disposal such that the packaging can be solubilized and sterilized in a single operation.

These and further objects will be more readily appreciated while considering the following disclosure and appended claims.

SUMMARY OF THE INVENTION

The present invention involves a water-soluble package comprising a container having an internal space defined by thermoplastic polymer side walls. The thermoplastic polymer side walls are capable of dissolving in water and aqueous solutions only at temperatures above approximately 37° C.

DETAILED DESCRIPTION OF THE INVENTION

The present invention deals with the disposal of packaging materials configured into diverse products including pouches which may have a significant transparent component to enable users to view the contents thereof. Further, as noted above, a good number of hospital procedures on contamination control encourage multi-barrier packaging and it is this type of configuration which also lends itself to the practice of the present invention.

It is contemplated that the water-soluble packaging of the present invention be composed of thermoplastic polymer side walls which are soluble in hot aqueous baths, including water, either alone or with the addition of surfactants, salts and bleaches. Such packaging would be insoluble in cold to warm baths, below 37° C., the average temperature of the human body. Preferably, the thermoplastic polymer would be soluble in aqueous media only above 50° C. and most preferably between 80°-90° C. At the latter temperature, packaging disposal could be accomplished in a hot water bath such as a washing machine that is dedicated solely to solubilizing and disinfecting such packaging made of such water soluble thermoplastic polymer. By employing such a method, two objectives will be accomplished; namely, that the packaging would be disinfected and would be solubilized for disposal through the sewer system. Not only would this lessen the burden now being imposed upon current landfill sites, but liquid sewer disposal would prove a comparative low cost technique of ridding the user of such packaging.

Polymer or sheet materials useful in practicing the present method comprise polyvinyl alcohol with or without acetyl groups, cross-linked or uncross-linked. Ideally, the packaging is comprised of polyvinyl alcohol homopolymer that has been highly crystallized by post drawing or heat annealing. Ideal for use in the present invention would be a highly crystallized totally saponified polyvinyl acetate. Suitable examples of commercially available materials for use in practicing the present invention include Vinex ™ 1003, a PVA polymer sold by Air Products Co. and Elvanol ™, a fully hydrolyzed PVA polymer sold by DuPont.

In producing packaging useful in practicing the present invention, a conventional textile carding machine can be employed whereby a web is laid down on a conveying structure that typically weighs approximately 50 grams per square yard. However, packaging materials generally should be in the range of 10 to 200 grams per square yard or more. More preferably, one should operate in the range of 20 to 100 grams per square yard while operating in the range of 30 to 70 grams per square yard is most convenient.

The web structure produced by the conventional textile carding machine is cross stretched, compressed and thermally bonded at a temperature near 200° C. across 50 percent or more of its face in a diamond or other pattern and may or may not be fully calendared to produce a stiff fabric structure. This fabric structure can then be die-cut into smaller pieces with and without the application of antistats, tints or fire retardants. These structures can then be cut into, for example, 9"×9" pieces which can be formed into a pouch either in a continuous manner or a batch manner that can hold medical instruments.

Pieces of the polymeric film and fabric, being thermoplastic, can be bonded together thermally. Polyvinyl alcohol behaves physically in a thermoplastic manner and is easily bonded by a Vertrod TM impulse heater system.

It is contemplated that films useful in practicing the present invention be between approximately 0.0005 to 0.030 inches in thickness for the heat impulse or thermal sealing of such side wall materials into a suitable pouch. More appropriately, one would use film thicknesses between approximately 0.001 to 0.006 inches and most conveniently, from approximately 0.002 to 0.004 inches.

It is contemplated that the term "packaging" be broadly construed to include not only pouches but any enveloping structure and particularly such a structure useful in maintaining a "sterile presentation." For example, the "packaging" can include procedural trays, such as anesthesia trays, suture removal trays, wound dressing trays, shave prep trays and I.V. administration trays which are used throughout patient treatment areas of hospitals, physicians' offices, dentists' offices and other health care sites which require sterile wraps and towels. Such wraps and towels are used not only for "sterile presentation" to the treatment site, but function as sterile fields during treatment and as towels for clean up work.

These "towel" products are carded and formed from suitable "textile" deniers (1-3 denier) in cut lengths (1-3 inches), calendared and thermoformed into 70-200 grams per square yard fabrics. Thermoforming is preferred for convenience, but other methods such as needle punching is certainly possible in practicing the present invention. A commercially available product for use in the present invention is either type T-B (VEE 1290) or type T-5 (VPB 101) wrap which are each available from Isolyser Company, Inc., which are manufactured of Kuralon's PVA fiber. Kuralon's PVA is sold in 44 mm lengths having a hot water solubility point of 80°-90° C. The T-B product is sized at 1.2 denier while the T-5 product is sold in 38 mm staple lengths of 1.5 denier.

We claim:

1. A method of disposing of packaging after the contents of the packaging has been removed, said packaging having an internal space defined by thermoplastic polymer side walls being capable of dissolving in water and aqueous solutions only at temperatures above approximately 37° C., said method comprising subjecting said packaging to water at sufficient temperature to substantially dissolve said thermoplastic polymer side walls whereupon said water and dissolved packaging are subjected to disposal said thermoplastic polymer comprising a polyvinyl alcohol homopolymer that has been crystallized by postdrawing or by heat annealing.

2. A method of disposing of packaging after the contents of the packaging has been removed, said packaging having an internal space defined by thermoplastic polymer side walls being capable of dissolving in water and aqueous solutions only at temperatures above approximately 37° C., and subjecting said packaging to water at sufficient temperature to substantially dissolve said thermoplastic polymer side walls whereupon said water and dissolved packaging are subjected to disposal said thermoplastic polymer comprising a polyvinyl alcohol that is produced from crystallized substantially totally saponified polyvinyl acetate.

3. A method of disposing of packaging after the contents of the packaging has been removed, said packaging having an internal space defined by thermoplastic polymer side walls being capable of dissolving in water and aqueous solutions only at temperatures above approximately 37° C., and subjecting said packaging to water at sufficient temperature to substantially dissolve said thermoplastic polymer side walls whereupon said water and dissolved packaging are subjected to disposal said thermoplastic polymer being approximately 10 to 200 grams per square yard in weight.

4. A method of disposing of packaging after the contents of the packaging has been removed, said packaging having an internal space defined by thermoplastic polymer side walls being capable of dissolving in water and aqueous solutions only at temperatures above approximately 37° C., and subjecting said packaging to water at sufficient temperature to substantially dissolve said thermoplastic polymer side walls whereupon said water and dissolved packaging are subjected to disposal said thermoplastic polymer being approximately 20-100 grams per square yard in weight.

5. A method of disposing of packaging after the contents of the packaging has been removed, said packaging having an internal space defined by thermoplastic polymer side walls being capable of dissolving in water and aqueous solutions only at temperatures above approximately 37° C., and subjecting said packaging to water at sufficient temperature to substantially dissolve said thermoplastic polymer side walls whereupon said water and dissolved packaging are subjected to disposal said thermoplastic polymer being approximately 30-70 grams per square yard in weight.

6. A method of disposing of packaging after the contents of the packaging has been removed, said packaging having an internal space defined by thermoplastic polymer side walls being capable of dissolving in water and aqueous solutions only at temperatures above approximately 37° C., and subjecting said packaging to water at sufficient temperature to substantially dissolve said thermoplastic polymer side walls whereupon said water and dissolved packaging are subjected to disposal and wherein a portion of said thermoplastic polymer side walls are substantially transparent so as to reveal the contents of said package before opening.

7. A method of disposing of packaging after the contents of the packaging has been removed, said packaging having an internal space defined by thermoplastic polymer side walls being capable of dissolving in water and aqueous solutions only at temperatures above approximately 37° C., and subjecting said packaging to water at sufficient temperature to substantially dissolve said thermoplastic polymer side walls whereupon said water and dissolved packaging are subjected to disposal said thermoplastic polymer side walls being substantially opaque.

* * * * *

REEXAMINATION CERTIFICATE (2911th)

United States Patent [19]
Honeycutt et al.

[11] B1 5,181,966
[45] Certificate Issued  *Jun. 11, 1996

[54] HOT WATER SOLUBLE PACKAGING MATERIALS

[75] Inventors: Travis W. Honeycutt, Gainesville; Robert L. Taylor, Jr., Roswell, both of Ga.

[73] Assignee: Isoyser Comp., Inc., Norcross, Ga.

[*] Notice: The term of this patent shall not extend beyond the expiration date of Pat. No. 5,207,837.

Reexamination Request:
No. 90/003,801, Apr. 24, 1995

Reexamination Certificate for:
Patent No.: 5,181,966
Issued: Jan. 26, 1993
Appl. No.: 907,777
Filed: Jun. 30, 1992

Related U.S. Application Data

[63] Continuation-in-part of Ser. No. 803,096, Dec. 5, 1991, abandoned, which is a continuation-in-part of Ser. No. 683,290, Apr. 10, 1991, abandoned.

[51] Int. Cl.$^6$ .............................. B08B 7/00; C11D 17/00
[52] U.S. Cl. ................................. 134/42; 252/90
[58] Field of Search .................. 134/42; 252/90, 252/92

[56] References Cited

U.S. PATENT DOCUMENTS

| | | | |
|---|---|---|---|
| 3,484,874 | 12/1969 | Bickenheuser, Jr. | 4/112 |
| 3,762,454 | 10/1973 | Wilkins, Jr. | 150/1 |
| 3,886,610 | 6/1975 | Shelden | 5/81 R |
| 5,051,222 | 9/1991 | Marten et al. | 264/143 |
| 5,181,967 | 1/1993 | Honeycutt | 134/42 |
| 5,207,837 | 5/1993 | Honeycutt | 134/42 |

FOREIGN PATENT DOCUMENTS

| | | |
|---|---|---|
| 8902229 | 1/1990 | Brazil . |
| 0050288 | 10/1981 | European Pat. Off. . |
| 0107576 | 5/1984 | European Pat. Off. . |
| 0176316 | 4/1986 | European Pat. Off. . |
| 0272816 | 6/1988 | European Pat. Off. . |
| 1519530 | 4/1970 | Germany . |
| 3017246 | 11/1981 | Germany . |
| 47-41741 | 10/1972 | Japan . |
| 55-71532 | 5/1980 | Japan . |
| 59-100704 | 6/1984 | Japan . |
| 60-44897 | 3/1985 | Japan . |
| 61-159995 | 7/1986 | Japan . |
| 2-68396 | 3/1990 | Japan . |
| 386161 | 1/1933 | United Kingdom . |
| 743165 | 1/1956 | United Kingdom . |
| 1187690 | 4/1970 | United Kingdom . |
| 1374199 | 11/1974 | United Kingdom . |
| 1451619 | 10/1976 | United Kingdom . |
| 2102461 | 2/1983 | United Kingdom . |
| 2119709 | 11/1983 | United Kingdom . |
| 2211196 | 6/1989 | United Kingdom . |
| 2211088 | 6/1989 | United Kingdom . |
| 2248842 | 4/1992 | United Kingdom . |
| WO91/14413 | 10/1991 | WIPO . |
| WO91/17210 | 11/1991 | WIPO . |

OTHER PUBLICATIONS

Hopper et al., Essentials of English, 4th ed., p. 223 (1990).
J. Brandrup et al., Polymer Handbook, 3rd ed., p. 435 (1989).
Plastics Compounding, 1993/1994, p. 41.
Encyclopedia of Polymer Science and Engineering, vol. 17, p. 192, John Wiley & Sons, Inc., New York (1989).

Primary Examiner—Zeinab El-Arini

[57] ABSTRACT

A water soluble package and its method of disposal. The package is provided with thermoplastic polymer side walls which are capable of dissolving in water and aqueous solutions only at temperatures above approximately 37° C.

B1 5,181,966

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–7 are determined to be patentable as amended.

New claims 8, 9–19 renumbered as 8–18 respectively are added and determined to be patentable.

1. A method of disposing of packaging after the contents of the packaging [has] *have* been removed, said packaging having an internal space defined by thermoplastic polymer side walls being capable of dissolving in water and aqueous solutions only at temperatures above approximately 37° C., said method comprising subjecting said packaging to water at sufficient temperature to substantially dissolve said thermoplastic polymer side walls whereupon said water and dissolved packaging are subjected to disposal said thermoplastic polymer comprising a polyvinyl alcohol homopolymer that has been crystallized by postdrawing or by heat annealing.

2. A method of disposing of packaging after the contents of the packaging [has] *have* been removed, said packaging having an internal space defined by thermoplastic polymer side walls being capable of dissolving in water and aqueous solutions only at temperatures above approximately 37° C., and subjecting said packaging to water at sufficient temperature to substantially dissolve said thermoplastic polymer side walls whereupon said water and dissolved packaging are subjected to disposal said thermoplastic polymer comprising a polyvinyl alcohol that is produced from crystallized substantially totally saponified polyvinyl acetate.

3. [A] *The* method of [disposing of packaging after the contents of the packaging has been removed, said packaging having an internal space defined by thermoplastic polymer side walls being capable of dissolving in water and aqueous solutions only at temperatures above approximately 37° C., and subjecting said packaging to water at sufficient temperature to substantially dissolve said thermoplastic polymer side walls whereupon said water and dissolved packaging are subjected to disposal] *claim 1, wherein* said thermoplastic polymer [being] *is* approximately 10 to 200 grams per square yard in weight.

4. [A] *The* method of [disposing of packaging after the contents of the packaging has been removed, said packaging having an internal space defined by thermplastic polymer side walls being capable of dissolving in water and aqueous solutions only at temperatures above approximately 37° C., and subjecting said packaging to water at sufficient temperature to substantially dissolve said thermplastic polymer side walls whereupon said water and dissolved packaging are subjected to disposal and] *claim 1, wherein said* thermoplastic polymer [being] *is* approximately 20–100 grams per square yard in weight.

5. [A] *The* method of [disposing of packaging after the contents of the packaging has been removed, said packaging having an internal space defined by thermoplastic polymer side walls being capable of dissolving in water and aqueous solutions only at temperatures above approximately 37° C., and subjecting said packaging to water at sufficient temperature to substantially dissolve said thermoplastic polymer side walls whereupon said water and dissolved packaging are subjected to disposal] *claim 1, wherein* said thermoplastic polymer [being] *is* approximately 30–70 grams per square yard in weight.

6. [A] *The* method of [disposing of packaging after the contents of the packaging has been removed, said packaging having an internal space defined by thermoplastic polymer side walls being capable of dissolving in water and aqueous solutions only at temperatures above approximately 37° C., and subjecting said packaging to water at sufficient temperature to substantially dissolve said thermoplastic polymer side walls whereupon said water and dissolved packaging are subjected to disposal and wherein] *claim 1, wherein* a portion of said thermoplastic polymer side walls are substantially transparent so as to reveal the contents of said package before opening.

7. [A] *The* method of [disposing of packaging after the contents of the packaging has been removed, said packaging having an internal space defined by thermoplastic polymer side walls being capable of dissolving in water and aqueous solutions only at temperatures above approximately 37° C., and subjecting said packaging to water at sufficient temperature to substantially dissolve said thermoplastic polymer side walls whereupon said water and dissolved packaging are subjected to disposal] *claim 1, wherein* said thermoplastic polymer side walls [being] *are* substantially opaque.

*8. The method of claim 1, wherein said packaging having an internal space defined by thermoplastic polymer side walls is capable of dissolving in water and aqueous solutions only at temperatures above 50° C.*

*9. The method of claim 1, wherein said packaging having an internal space defined by thermoplastic polymer side walls is capable of dissolving in water and aqueous solutions only at temperatures between 80°–90° C.*

*10. The method of claim 1, wherein the polyvinyl alcohol homopolymer has been crystallized by post-drawing.*

*11. The method of claim 1, wherein the polyvinyl alcohol homopolymer has been crystallized by heating annealing.*

*12. The method of claim 1, wherein the packaging is made from a film.*

*13. The method of claim 1, wherein the packaging is made from a fabric.*

*14. The method of claim 1, wherein the packaging is a medical procedural tray.*

15. The method of claim 1, wherein the crystallized polyvinyl alcohol is produced from substantially totally saponified polyvinyl alcohol.

16. The method of claim 2, wherein the polyvinyl alcohol has been crystallized by post-drawing.

17. The method of claim 2, wherein the polyvinyl alcohol has been crystallized by heat annealing.

18. The method of claim 2, wherein the polyvinyl alcohol has been crystallized by post-drawing or by heat annealing.

* * * * *